United States Patent [19]

Alderman et al.

[11] Patent Number: 4,879,222

[45] Date of Patent: Nov. 7, 1989

[54] METHOD OF ISOLATING TUMOR-SECRETED PRODUCTS USING A NOVEL PROTEIN-FREE MEDIUM

[75] Inventors: Edward M. Alderman, Dedham; James W. Fett, Waltham; Bert L. Vallee, Brookline, all of Mass.

[73] Assignee: President and Fellows of Harvard College, Cambridge, Mass.

[21] Appl. No.: 901,101

[22] Filed: Aug. 28, 1986

[51] Int. Cl.[4] .................... C12P 21/00; C12N 05/00
[52] U.S. Cl. ................... 435/68; 435/240.23; 435/240.31
[58] Field of Search ............... 435/240.23, 68, 240.31

[56] References Cited

U.S. PATENT DOCUMENTS 4,217,412 8/1980 Tolbert et al. .
4,228,236 10/1980 Jakstys et al. .................. 435/240.25
4,456,550 6/1984 Dvorak et al. .

OTHER PUBLICATIONS

Alderman et al, Proc. Natl. Acad. Sci. 82, pp. 5771–5775 (Sep. 1985).
Fett et al, Biochemistry 24, pp. 965–975 (Feb. 1985).
ReChclgl, CRC Handbook Series in Nutrition and Food, Section G, vol. IV, CRC Press, Cleveland, Ohio, pp. 33, 42 and 106–110 (1977).
Murakami et al., Proc. Natl. Acad. Sci. 77(6) p. 3464–8 (1980).

*Primary Examiner*—John Tarcza
*Attorney, Agent, or Firm*—Allegretti & Witcoff, Ltd.

[57] ABSTRACT

A medium for the maintenance of mammalian anchorage-dependent colonic adenocarcinoma cells comprising a solution of an effective maintenance amount of buffered salts, L-glutamine and glucose, which is devoid of exogenous protein. The medium further includes a solution containing amino acids.

3 Claims, 3 Drawing Sheets

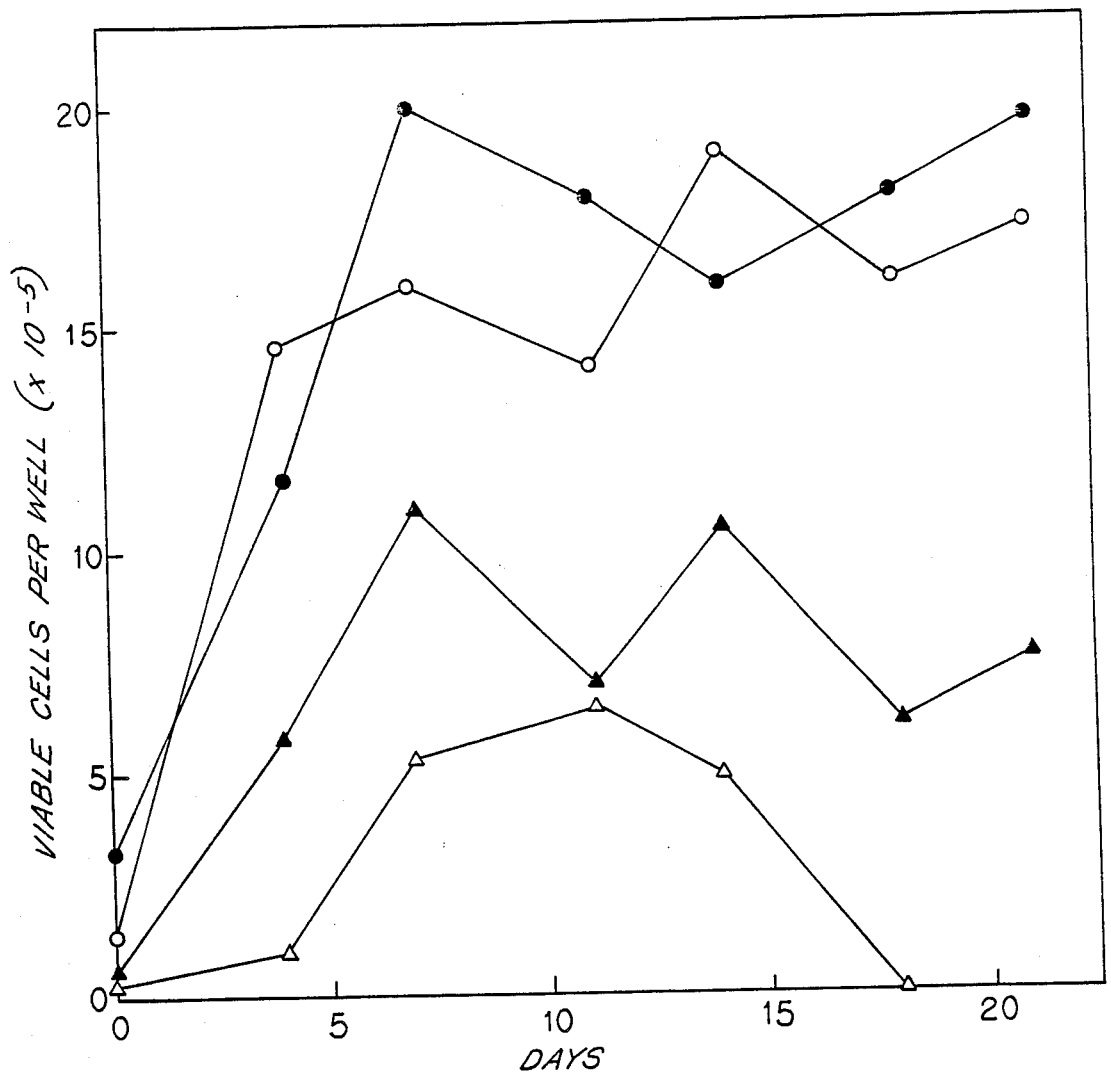

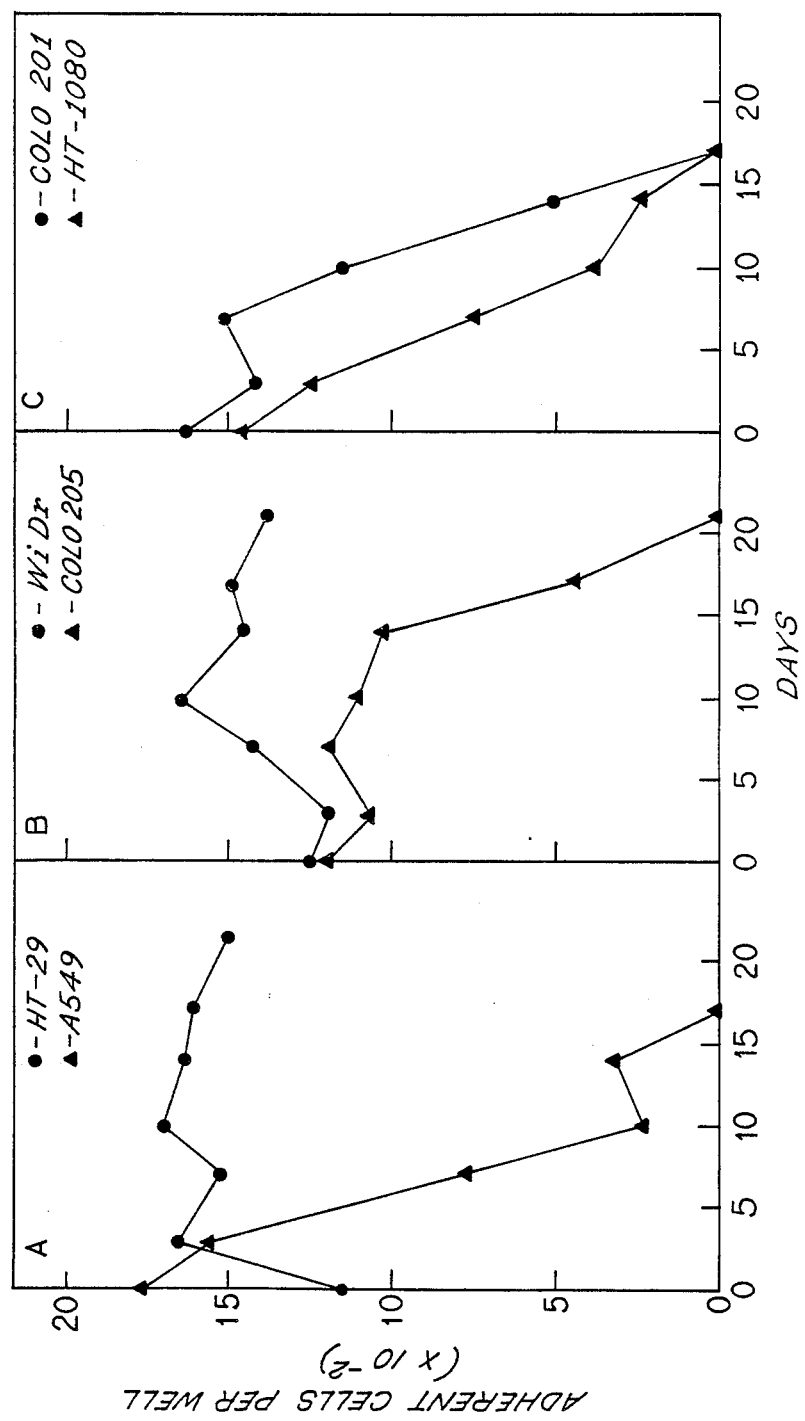

METHOD OF ISOLATING TUMOR-SECRETED PRODUCTS USING A NOVEL PROTEIN-FREE MEDIUM

BACKGROUND OF THE INVENTION

1. Field of the Invention

This invention relates to a novel protein-free maintenance medium for mammalian tumor cells. This invention further relates to a method of isolating tumor-secreted products using said maintenance medium.

2. Description of Related Art

Tumor-secreted products play critical roles in malignant growth. They subserve a multitude of functions including interference with the host immune response (North et al., *J. Exp. Med.* 143, 559–573 (1976); Veit et al., *J. Immunol.* 117, 655–660 (1976)), autostimulation of tumor cell growth (Sporn et al., *New Engl. H. Med.* 303, 878–880 (1980); Kaplan et al., *Proc. Natl. Acad. Sci. USA* 79, 485–489 (1982), modulation of invasion and metastasis (Goldfarb, R. N., in *Tumor Invasion and Metastasis*, eds. Liotta & Hart (Martinus Nijhoff, The Hague), pp. 375–390 (1982) and induction of neovascularization (Folkman, J., *Adv. Cancer Res.* 19, 331–358 (1974); Vallee et al., *Experientia* 41, 1–15 (1985)). The chemical and biological characterization of such molecules provide valuable insight into the mechanisms governing the complex biological processes of malignancy while also providing new means for cancer detection, diagnosis and therapeutic management. The identification as well as the structural and functional characterization of such molecules depends critically on the availability of systems from which such molecules can be isolated in high yield. While in vitro cultivation of established tumor lines remains the method of choice, it is laborious to purify tumor-secreted products to homogeneity from such cultures. This is due, in part, to the typical serum requirements of most cells, since its presence complicates the purification of such products.

The large-scale, in vitro cultivation of malignant cells can potentially produce tumor-derived biomolecules in yields sufficient for both biological and chemical characterization. However, for this purpose, exogenous serum and/or its growth factor components are virtually compulsory additives. Serum supplies growth factors, hormones, transport and attachment factors, or lipids whose nature, amounts or mechanisms of action remain largely unspecified. For example, Dulbecco's modified Eagle's medium (Whittaker M. A. Bioproducts, Walkersville, Md.) plus small amounts of glutamine, around 2 mM, has been studied in presence of serum and other proteins as a growth medium. Studies provide evidence that glutamine serves as a major energy source, not only for normal cells in vivo, but also for tumor cells cultivated in vitro. Energy provisions through glutamine utilization has been described for several tumor types which include HeLa, lymphoma and myeloma cells (Reitzer et al., *J. Biol. Chem.* 254, 2669–2676 (1979); Lavietes et al., *Proc. Natl. Acad. Sci. USA* 71, 3993–3997 (1974); Roberts et al., *J. Cell Sci.* 21, 609–615 (1976)). Moreover, increased glutamine utilization has been shown to correlate with malignant growth in vivo (Kovacevic et al., *Cancer Res.* 32, 326–333 (1972); Aaki et al., *J. Biol. Chem.* 257, 432–438 (1982)).

Techniques for cultivating both primary and established lines of mammalian tumor cells in serum-free but supplemented medium are well known. Such media can provide a suitable environment for cell proliferation but with a few exceptions (Healy et al., *Proc. Soc. Exp. Biol. Med.* 89, 71–77 (1955); Merchant et al., *Proc. Soc. Exp. Biol. Med.* 110, 194–198 (1962); Agy et al., In Vitro 17, 671–680 (1982); Kaighn et al., *Proc. Natl. Acad. Sci. USA* 78, 5673–5676 (1981) require supplementation with various hormones and proteins (Barnes et al., *Anal. Biochem* 102, 255–270 (1980)). Further, each new cell type usually requires an unique, defined medium for serum-free growth. The nutrient requirements of quiescent but actively metabolizing cells are typically much less than those needed for proliferation of cells (Ham, R. G., in *Tissue Growth Factors*, ed. Baserga, R. (Springer-Verlag, New York), pp. 13–74 (1981)).

Nevertheless, the addition of serum and other protein supplements has greatly complicated the procedure itself and, beyond that, the very objective, i.e., the identification and purification of tumor constituents which are usually present in vanishingly small amounts. Successful attempts as culturing tumor cells under serum-free conditions have been reported, but, while eliminating addition of serum, they usually have substituted such moieties obtained from it (Barnes et al., *Anal. Biochem*, 102, 255–270 (1980); Higuchi, K., *Adv. Appl. Microbiol.* 16, 111–136 (1973); Ham, R. G., in *Tissue Growth Factors*, ed. Baserga, R. (Springer-Verlag, New York, pp. 13–74 (1981)). Moreover, each cell line generally then requires a set of molecular species unique for its survival and devised to bring about cellular proliferation rather than maintenance of longterm viability and secretory capacity. As for normal cells, long-term survival in serum-free media has not been shown. By way of illustration, Hanks' Balanced Salt Solution (Whittaker M. A. Bioproducts, Walkersville, Md.) containing inorganic salts and glucose is used only as a transport medium to sustain normal cell viability and metabolism at reduced temperatures, around 4° C., for extremely short periods of time, up to around 24 hours (Hanks et al., *Proc.Soc.Exp. Biol. Med.* 71, 196–200 (1949)). Other investigators have demonstrated survival of certain tumor cell lines or only 2–3 days with serum-free modified Eagle's medium (Iwata et al., *Cancer Res.* 45, 2689–2694 (1985); Moses et al., *Cancer Res.* 41, 2842–2848 (1981)). The ability to obtain long-term survival and retain secretory capacity has proven difficult, if not impossible, to achieve in protein-free media.

The addition of 2 mM, L-glutamine to serum-free Dulbecco's modified Eagle's medium containing 4.5 mg/mL of glucose, inter alia, has been described for use as a maintenance medium for HT-29 cell cultures in Fett et al., *Biochemistry* 24, 965–975 (1985), but this medium does not preserve both the long-term viability and firm attachment of cells in large-scale cultures.

Dvorak et al. U.S. Pat. No. 4,456,550 describes the use of Dulbecco's modified Eagle's medium having a glucose content of 4 g/l, inter alia, as a medium for Line 10 tumor cells, but the medium lacks L-glutamine. Tolbert et al. U.S. Patent No. 4,217,412 describes a culture medium of Dulbecco's modified Eagle's medium to which are added 4 mg/mL glucose and known essential amino acids, mineral salts, vitamins, and carbohydrates can be substituted for it in growing TE-671 cells; there is no mention of L-glutamine.

Alderman et al., *Proc.Natl.Acad.Sci.*, USA 82, 5771–5775 (September, 1985) describes the medium of the present invention.

Unexpectedly, it has been found that 5 mM L-glutamine is sufficient to preserve both the long-term viability and firm attachment of cells in large-scale cultures that are free of exogenous protein, using the maintenance medium described herein, whereas 2 mM L-glutamine in the same medium is shown to be ineffective.

SUMMARY OF THE INVENTION

It is therefore an important object of the present invention to provide an in vitro protein-free maintenance medium with optimal conditions for mammalian tumor cells.

Another object is to provide a protein-free maintenance medium for longterm viability of mammalian tumor cells.

A further object is to provide a protein-free maintenance medium that minimizes the amount of cell proliferation, thus obviating the necessity for subculturing.

A still further object is to provide a defined protein-free maintenance medium that does not need serum or protein supplements thereby making handling of mammalian tumor cells easier and facilitating the identification of the tumor-secreted products from the cells.

Another further object is to provide a protein-free maintenance medium that has the ability to generate continuously important tumor-derived products in large-scale cultures so these products can be isolated readily from the conditioned medium devoid of exogenous protein.

Further purposes and objects of the present invention will appear as the specification proceeds.

With the foregoing and other objects in view, the invention herein provides a protein-free maintenance medium for mammalian tumor cells. The background of the invention and its departure from the art will be further described hereinbelow.

BRIEF DESCRIPTION OF THE DRAWINGS.

The background of the invention and its departure from the art will be further described hereinbelow with reference to the accompanying drawings, wherein:

FIG. 2 shows the population-dependent growth of HT-29 cells in a protein-free medium of the present invention; and FIG. 3 shows a comparison of growth for several tumor cell lines in a protein-free medium of the present invention.

DETAILED DESCRIPTION OF THE PREFERRED EMBODIMENTS

Figure 1:
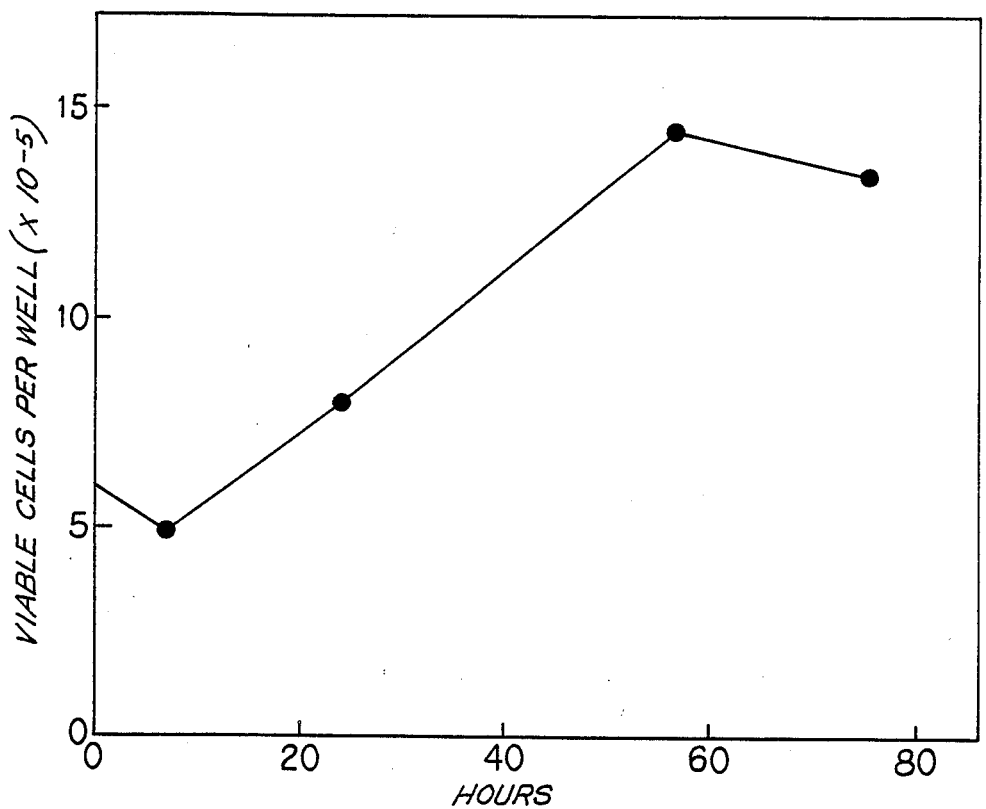
FIG. 1 shows the short-term growth curve of HT-29 cells in a protein-free medium of the present invention.

The present invention concerns a protein-free maintenance medium for mammalian tumor cells optimized for cell survival and the maintenance of secretory capacity. Maintaining long-term viability rather than proliferation of human tumor cells in serum-free media and in the absence of serum associated factors greatly enhances the ability to isolate and characterize tumor-secreted products. The maintenance medium of this invention is devoid of exogenous proteins or other growth factors and supports the survival of tumor cells. A medium that supports cell viability but not proliferation permits long-term harvesting of secreted products without the need for extensive manipulation and subculturing of cells. The maintenance medium obviates the difficulties involved in isolating products synthesized in very low yield from large amounts of protein added to the medium for growth.

The protein-free maintenance medium of this invention comprises a solution of buffered salts containing concentrations of about 5 mM to about 12 mM, preferably 5 mM, of L-glutamine and about 0.1 g to about 5 g per liter of glucose. The solution of buffered salts contains inorganic salts in an effective maintenance amount which approximates the concentrations normally found in growth media. Typical inorganic salts include, but are not limited to calcium chloride, potassium chloride, sodium chloride, sodium bicarbonate, sodium biphosphate, sodium dihydrogen phosphate, potassium dihydrogen phosphate, ferric nitrate, magnesium sulfate and the like. A second preferred embodiment of this invention is a maintenance medium comprising a solution of buffered salts containing concentrations f about 5 mM to about 12 mM of L-glutamine, an amino acid and about 0.1 g to about 5 g per liter of glucose. The amino acids include, but are not limited to, L-arginine, L-cystine, glycine, L-histidine, L-isoleucine, L-leucine, L-lysine, L-methionine, L-phenylalanine. L-serine, L-threonine, L-tryptophan, L-tyrosine and L-valine. The medium contains an effective maintenance amount of one or more amino acids which equals the typical concentrations found in growth media. To this latter formulation, vitamins may be added to comprise a third embodiment. Such vitamins are, for example, D-calcium pantothenate, choline chloride, folic acid, I-inositol, nicotinamide, pyridoxal, riboflavin, thiamine, etc.

Optionally, a pH indicator (e.g., phenol red), a feedback inhibitor of glycolysis (e.g., sodium pyruvate), antibiotic agents (e.g., gentamycin sulfate, penicillin-streptomycin mixture) and antifungal agents (e.g., amphotericin B) may be added in appropriate amounts to the maintenance medium of this invention. In addition to these examples, other conventional pH indicators, supplemental feedback inhibitors of glycolysis, antibiotic agents and antifungal agents are contemplated to be included within the scope of this invention.

A particularly preferred embodiment of the present invention is a maintenance medium comprising Dulbecco's modified Eagle's medium (Whittaker M.A. Bioproducts) containing 4.5 g/L of glucose supplemented with about 5 mM to about 12 mM, preferably 5 mM, of L-glutamine. Optionally, about 5 mcg/L to about 10 mcg/L, preferably 5 mcg/L, of amphotericin B and about 50 mg/L to about 100 mg/L, preferably 50 mg/L, of gentamycin sulfate may be added to this maintenance medium.

The invention herein also encompasses a method for maintaining mammalian anchorage-dependent colonic adenocarcinoma cells which comprises maintaining the cells in a maintenance medium containing about 5 mM to about 12 mM of L-glutamine and devoid of exogenous protein for more than ten days. This invention further involves a method of isolating a mammalian tumor-secreted product which comprises maintaining mammalian anchorage-dependent colonic adenocarcinoma cells in the maintenance medium devoid of exogenous protein for more than ten days and isolating the tumor-secreted product from the medium.

For purposes of this invention, a maintenance medium is a modified or conditioned growth medium devoid of exogenous protein yet capable of sustaining metabolically active cells in vitro with minimal cellular proliferation for periods exceeding ten days, preferably thirty days. The term survival in this context means that at least one-half of the cell population is viable by the tenth day. The protein-free maintenance medium defined herein supports the survival of tumor cell lines, most notably, established human colonic adenocarcinoma cell lines in vitro, i.e., HT-29, WiDr, COLO 201 and COLO 205, which remain physiologically active with respect to some functions. With respect to the HT-29 cells, the maintenance medium specified above as the particularly preferred embodiment of this invention permits long-term survival of greater than 120 days. Viability is dependent upon both the concentration of L-glutamine in the medium and the cell density at the time of initial transfer into it.

The limiting conditions for the maintenance medium described herein are inherent in the particular tumor cell line and would be readily apparent to those persons skilled in the art. For example, for the HT-29 line, cell density at the time of shift is a critical consideration for survival. This observation, which has been reported in other serum-free systems (Agy et al., *In Vitro* 17, 671–680 (1981); Kaighn et al., *Proc. Natl. Acad. Sci. USA* 78, 5673–5676 (1981); Todaro et al., *Proc Natl. Acad. Sci. USA* 77, 5258–5262 (1980)), strongly suggests that nutrients and/or hormone-like substances produced by the tumor cells themselves are required for cellular maintenance even in the presence of added glutamine. Such growth promoting substances have been described and isolated from animal and human tumor sources (Todaro et al., *Proc. Natl. Acad. Sci. USA* 77, 5258–5262 (1980); DeLarco et al., *Proc. Natl. Acad. Sci. USA* 75, 4001–4115 (1978)), and, importantly, potent growth factor activity has been found in the HT-29 serum-free conditioned medium of this invention (see Table 3). Autologous conditioned medium is thus required for protein-free passage of HT-29 cells. A minimal concentration of 7% carbon dioxide gas is also required to be maintained over the culture for the maintenance phase. Additionally, only anchoragedependent tumor cells may be capable of long-term survival in the maintenance medium of this invention, since all attempts at maintaining HT-29 and WiDr cells adapted to suspension culture in protein-free medium have been unsuccessful. Nevertheless, one skilled in the art can select from any tumor cell line for anchoring ability and then use these anchorage-dependent cells in the process of this invention.

Although four established colonic adenocarcinoma cell lines can be maintained in the protein-free maintenance medium of this invention under the conditions described, the lung carcinoma and fibrosarcoma lines did not survive (FIG. 3). Nevertheless, the data do suggest that it may be possible to maintain yet other cell lines if they are transferred at high density into the maintenance medium.

Mammalian tumor cells can be maintained in a viable state in the protein-free medium of this invention and have been found to not require serum for long-term survival. Large-scale, protein-free cultivation of tumor cells conveniently allows for the generation of important tumor-secreted products in antigenically pure form. For purposes of this invention, pilot-scale cultivation is cultivation in vessels where ease of evaluation of cell count is maximized, and in which medium throughput is on the order of five milliliters/week per vessel, whereas large-scale cultivation is cultivation in cell factories, which are intended to grow and maintain cells efficiently with a minimum of medium, and in which medium throughput is on the order of five liters/week per factory. Around five liters of conditioned medium per week can be harvested from each cell factory maintained according to the method of this invention. Minimal harvesting and re-feeding is required since cell proliferation is negligible and subculturing is not necessary. A number of secreted, tumor-derived products may be detected. For example, HT-29 adenocarcinoma cells maintained in large-scale culture with this medium continue to secrete the established colon tumor marker carcinoembryonic antigen (CEA) as well as 3T2 cell growth factors and lysozyme. HT-29 cells synthesize and secrete large amounts of lysozyme (Fett et al., *Biochemistry* 24, 965–975 (1985)) which provides a convenient marker of cellular secretory capacity. Additionally, several other molecules have been identified and partially purified from the protein-free medium of HT-29 cells. These include $\beta_2$-microglobulin, an angiogenic factor and a vascular permeability factor.

In the past, attempts to isolate some of these biological factors failed because they are secreted in minuscule amounts making isolation, purification and characterization difficult in the presence of serum and protein supplements. The medium of the present invention overcomes this problem by eliminating the need for serum or protein and by providing a maintenance medium from which large quantities of tumor-secreted proteinaceous substances can readily be isolated, purified and identified. Once the amino acid sequence of the protein is known and characterized, it can be prepared by conventional genetic engineering techniques. Such techniques may involve coding a DNA segment to produce the protein in the proper sequence or other techniques well known in the art. Active portions of the protein can be identified and produced using the same conventional methods.

The identification of tumor-secreted products is useful for developing new means for early detection, diagnosis and therapeutic management of cancer. The chemical and biological characterization of the products provides a determination of the mechanism for the carcinogenic effect. For diagnostic purposes, early metabolites of tumor cells could be detected by conventional assays and analytical techniques. The by-products may be traced back to the gene in the tumor cell thereby permitting design of appropriate drugs to block or neutralize the cites of origin for cancer activity. Peptides prepared by the above techniques may serve as antigens for the production of monoclonal and polyclonal antibodies. Moreover, the amino acid analysis and sequence information may be useful in making synthetic peptides for generation of antibodies and making DNA probes. Preparation of the peptides may lead to developing vaccines or therapeutic agents.

The following examples demonstrate certain aspects of the present invention. However, it is to be understood that these examples are for illustrative purposes only and do not purport to be wholly definitive as to conditions and scope o this invention. All parts and percents referred to herein are on a weight basis and all temperatures are expressed in degrees Celsius unless otherwise specified. The term mM means concentration in millimolar, that is, millimoles per liter. It also should be appreciated that when typical reaction conditions (e.g., temperature, reaction times) have been given, the conditions which are both above and below these specified ranges can also be used, though generally less conveniently.

A further understanding of the invention may be obtained from the following nonlimiting examples. In these examples, all incubations were at about 35° to about 37° C. and atmospheric pressure, and all other operations were conducted at room temperature (about 23° to about 28° C.) and at atmospheric pressure.

EXAMPLE 1

Propagation and Maintenance of Tumor Cell Lines

All tumor cells were of human origin and included the colorectal adenocarcinoma lines HT-29 (deposited with American Type Culture Collection under accession number ATCC-HTB 38) (Fogh et al. (1975) in *Human Tumor Cells in Vitro*, ed. Fogh, J. (Plenum, New York), pp. 115–160), WiDr (deposited with American Type Culture Collection under accession number ATCC-CCL 218), COLO 201 (deposited with American Type Culture Collection under accession number ATCC-CCL 224), and COLO 205 (deposited with American Type Culture Collection under accession number ATCC-CCL 222); the lung carcinoma line A549 (deposited with American Type Culture Collection under accession number ATCC-CCL 185); and the fibrosarcoma line HT-1080 (deposited with American Type Culture Collection under accession number ATCC-CCL 121). Cells were propagated routinely in T-flasks (Costar, Cambridge, MA) as monolayer cultures using Dulbecco's modified Eagle's medium (Whittaker M.A. Bioproducts, Walkersville, Md.) (*Virology* 8, 396–397 (1959)) containing 4.5 mg/ml glucose, 50 $\mu$g/ml gentamycin sulfate, and 0.5 $\mu$g/ml amphotericin B (DME) and supplemented with 5% heat inactivated fetal bovine erum (FBS) and 2 mM L-glutamine (DME/5). Balb/c 3T3 cells, clone A31 (deposited with American Type Culture Collection under accession number ATCC-CCL 163) was treated according to conventional methods of Klagsbrun et al., *Exp. Cell Research* 105, 99–108 (1977), to provide subculture MK25. Balb/c 3T3 cells, clone A31-MK25 were maintained in DME supplemented with 2 mM L-glutamine and 10% heat inactivated bovine serum. Cultures were incubated at 37° C. or about 5–8 days in humidified air maintained at 7% $CO_2$. Cells were fed every 2–3 days as required and subcultured at confluence employing standard trypsinization techniques.

EXAMPLE 2

Evaluation of Cell Growth in Serum-Free Medium and Medium Containing FBS

To evaluate HT-29 growth in serum-free medium, cells maintained as above were trypsinized, resuspended in DME/5, and plated into 24-well (1.9 $cm_2$) Nunc microplated (Vangard International, Inc., Neptune, N.J.) at $1 \times 10^5$ cells/well. At specified cells harvested with trypsin. Cells were counted microscopically after vital staining with acridine orange/ethidium bromide. Duplicate wells were counted and average values calculated. In some instances, conditioned medium was harvested and non-adherent cells counted as above. Remaining cultures were re-fed with 1 ml of protein-free medium comprising DME as described in Example 1 supplemented with 5 mM L-glutamine.

Protein-free maintenance of other cell lines was evaluated by plating cells at densities of $1 \times 10^5$/ml in 100 $\mu$l of DME/5 into 96-well, half-area (0.15 $cm^2$) microplates (Costar). At levels approaching confluence, i.e., around $1.2 \times 10^5$ cells per $cm^5$, cultures were transferred into protein-free medium and re-fed as indicated. Adherent cells were counted using automated cell counting techniques. Twelve wells were counted per data point and the average of these counts calculated.

EXAMPLE 3

Evaluation of Protein-Free Maintenance Medium Containing Various Concentrations of L-glutamine on Pilot Scale Cultures Protein-free medium was supplemented respectively with 2 mM, 5 mM, 7 mM, 10 mM and 15 mM of L-glutamine to discern its effect n cell growth and suvival. The data (Table 1) depicting adherent cell counts on days 3, 7 and 31 demonstrate that addition to DME of 5 mM L-glutamine (DME/5 mM GLN) supported the survival of the greatest number of viable cells over the 31 day period. There was no significant advantage gained by the addition of greater quantities of L-glutamine up to 15 mM. This was subsequently found to be independent of the cell concentration at the time of transfer into protein-free, L-glutamine supplemented DME. In no instance did the percentage of non-viable adherent cells exceed 5%. Moreover, when non-adherent cells were similarly counted in cultures maintained in DME/5 mM GLN, they were found to amount to about 1% of the total adherent population and to be more than 90% viable. The non-adherent population remains essentially constant throughout the course of this procedure just as the adherent population. These findings indicate that under the stated conditions, i.e., transfer into DME/5 mM GLN, HT-29 cell proliferation is minimal and a dynamic cellular proliferation balanced by cell death does not occur.

TABLE 1

Effects of L-glutamine on protein-free growth of HT-29 cells in 2 $cm^2$ culture vessels

| Supplements to DME | Viable cells per well ($\times 10^{-6}$) | | |
|---|---|---|---|
| | Day 3 | Day 7 | Day 31 |
| 2 mM L-glutamine | 0.8 | 2.0 | 1.7 |
| 5 mM L-glutamine | 0.8 | 2.2 | 2.8 |
| 7 mM L-glutamine | 0.7 | 1.2 | 2.1 |
| 10 mM L-glutamine | 0.7 | 1.6 | 2.1 |
| 15 mM L-glutamine | 0.5 | 1.4 | 1.3 |

Cells were plated at $1 \times 10^5$ per 1.9-$cm^2$ well and grown to $14.5 \times 10^5$ cells per well. At this time (day 0) medium was replaced with 1 ml of DME supplemented as above. Medium was subsequently replaced twice weekly. Data presented are viable adherent cell counts (average of duplicate wells) on days 3, 7, and 31.

EXAMPLE 4

Preparation of Large-Scale, Protein-Free Cultures

HT-29 cells, maintained as above in Example 1, were seeded into a 6,000 $cm^2$ Nunc multi-level cell factory (Vangard International, Inc.) using an inoculum of $1 \times 10^8$ cells in 1.5 L of DME/5. At 80–90% confluence (3–5 days), the standard growth medium was replaced with 1.5 L of protein-free maintenance medium of DME supplemented with 0.2 mM, 5 mM and 10 mM of L-glutamine, respectively. Conditioned medium was harvested at two to three day intervals and clarified by sequential passage through Whatman 40 filter paper and Whatman 934-AH glass microfiber filters. The resulting serum-free conditioned medium (SFCM) was frozen and stored at −20° C. for subsequent evaluation. Factories were re-fed after each harvest with 1.5 L of freshly prepared protein-free medium.

DME supplemented with 0 or 2 mM of L-glutamine was not effective in maintaining large-scale cultures of adherent HT-29 cells (Table 2). Under these conditions, the monolayer detached and was lost upon harvest of conditioned medium within eight days of shifting to maintenance medium. In contrast, HT-29 monolayers remained viable and firmly attached throughout the experimental period (30–120 days), when maintained in DME supplemented with 5 mM of 10 mM of L-glutamine.

TABLE 2

Effects of L-glutamine on large-scale maintenance of HT-29 cells
HT-29 confluence (%)

| DME with supplementary L-glutamine (mM) | Day 2 | Day 4 | Day 7 | Day 10 | Day 30 |
|---|---|---|---|---|---|
| 0 | 80 | 20 | 0$^a$ | — | — |
| 2 | 90 | 70 | 20 | 0$^a$ | — |
| 5 | 95–99 | 95–99 | 95–99 | 95–99 | 95–99 |
| 10 | 95–99 | 95–99 | 95–99 | 95–99 | 95–99 |

Cells were plated at 1 to 2 × 10$^8$ per 6000 cm$^2$ cell factory and grown to 80 to 90% confluence (three to five days), then the growth medium was replaced with 1.5 L protein-free maintenance medium supplemented with L-glutamine as indicated (day zero). Estimates of confluence were made microscopically upon refeeding each factory at two to three day intervals.
$^a$Monolayers detached and were lost upon harvest of conditioned medium.

EXAMPLE 5

Evaluation of SFCM for Extracellular Products

Bovine serum albumin and carcinoembryonic antigen (CEA) were quantitated by the rocket immunoelectrophoretic method of Laurell (Laurell, C. B., *Anal. Biochem.* 15, 45–52 (1966)) using the appropriate rabbit antiserum (Accurate Chemical and Scientific Corp., Westburg, N.Y.). The CEA used as a standard was obtained from Calbiochem-Behring (San Diego, Calif.). Lysozyme activity was determined spectrophotometrically according to the turbidometric method of Locquet et al., *Biochem. Biophys. Acta* 167, 150–153 (1968). Growth factor activity was determined by stimulation of quiescent confluent monolayers of 3T3 cells (Lobb et al., *Biochemistry* 23, 6295–6299 (1984)). Prior to the growth factor and CEA assays, SFCM was dialyzed versus deionized (pyrogenfree) water using 6,000 to 8,000 molecular weight cutoff tubing (Spectra/Por) and concentrated 100-fold by lyophilization and reconstitution.

EXAMPLE 6

Selectivity of Competent Subpupulation of Adherent Cells in DME/5 mM GLN

HT-29 cells were plated into 24-well microplates using 1 ml cultures containing 1×10$^5$ HT-29 cells per 1.9 cm$^2$ well in DME/5 and grown to a density of 6×10$^5$ cells per well. Cultures were re-fed at this time (day 0) with 1 ml of DME/5 mM GLN and adherent cells were harvested and counted at 7, 24, 56, and 75 hours. Data were presented as the average of duplicate wells. There was no significant initial loss of adherent cells. Non-viable cells did not exceed 5% of the total adherent cell population. After a short lag period, cells continued to divide until the culture approached confluence and a growth plateau was reached. There was no initial selective event favoring a competent subpopulation of adherent cells upon transfer into DME/5 mM GLN (see FIG. 1).

EXAMPLE 7

Density Dependency of Survival in DME/5 mM GLN

HT-29 cells were plated at 1×10$^5$, 5×10$^4$, 1×10$^4$, and 5×10$^3$ cells per 1.9 cm$^2$ well in 1 ml of DME/5 and allowed to grow for 72 hours. At this time, i.e., day 0, medium was replaced with 1 ml of DME/5 mM GLN. As above, adherent cells were harvested and counted. Remaining wells were re-fed with protein-free medium. Medium was replaced in remaining wells twice weekly. Data are the average of duplicate wells. Non-viable cells did not exceed 6% of the total adherent cell population. FIG. 2 shows that a critical population density of HT-29 cells at the time of transfer into protein-free maintenance medium is required to sustain survival beyond 18 days. At a threshhold level of around 2×10$^4$ cells per cm$^2$, HT-29 cells can be maintained, but below this level, long-term survival cannot be achieved. This is in constrast to culture of HT-29 cells in DME/5 where clonal growth was observed.

EXAMPLE 8

Large-Scale Cultivation and Evaluation of Extracellular Products Secreted From HT-29 Cells Large-scale cultivation of HT-29 cells was initiated according to the procedure of Example 4 to provide sufficient amounts of conditioned medium to examine extracellular products. Two factories were maintained for four weeks and the average lysozyme, growth factor activity for 3T3 cells, and CEA levels determined throughout this period (Table 3). There appeared to be no initial loss of lysozyme secretory capacity when cells were placed in serum-free medium. This was determined by comparing the lysozyme value at day 0, i.e., conditioned medium harvested before transfer into DME/5 mM GLN, with those obtained for subsequent harvests, although values did tend to decrease with time. Conditioned medium obtained at days 7, 14, 21 and 28 also contained growth factor activity. Harvests at day 0 and 2 were not examined for this activity since FBS and, hence, serum-derived growth factors were still expected to be present (Antoniades et al., *Proc. Natl. Acad. Sci. USA* 72, 2635–2639 (1975)). By day 7, however, FBS-derived albumin could not be detected immunochemically in the SFCM (limit of detection is around 200 ng/ml). Additionally, SFCM contains immunochemically detectable amounts of the HT-29 product, CEA (Egan et al., *J. Natl. Cancer Inst.* 49, 887–889 (1972)). As in the case of lysozyme, growth factor activity and CEA levels decreased with time. Thus, HT-29 cells maintained under the specified protein-free conditions not only survived longterm but, importantly, they retained their capacity to secrete tumor-derived products. As shown in Table 3, the yield of extracellular, tumor-derived products decreased with time and, as a consequence, factories were routinely replaced after sixty days.

TABLE 3.

Release of lysozyme, CEA, and growth factor(s) during protein-free maintenance of HT-29*

| Day | Lysozyme (ng/ml) | CEA (ng/ml) | 3T3 activity (units per ml) |
|---|---|---|---|
| 0+ | 352 | 77 | ND± |
| 2 | 300 | 63 | N± |
| 7 | 435 | 70 | 0.55 |

TABLE 3.-continued

Release of lysozyme, CEA, and growth factor(s) during protein-free maintenance of HT-29*

| Day | Lysozyme (ng/ml) | CEA (ng/ml) | 3T3 activity (units per ml) |
|---|---|---|---|
| 14 | 381 | 52 | 0.37 |
| 21 | 182 | 35 | 0.30 |
| 28 | 154 | 35 | 0.28 |

*Data are the average values obtained from two separate factories.
+Conditioned medium containing FBS harvested before transfer into DME/5mM GLN.
±Not determined due to expected presence of FBS-derived growth factors (see text).

EXAMPLE 9

Protein-Free Culture of Other Cell Lines

Three colon carcinoma lines (WiDr, COLO 201, COLO 205), one lung carcinoma line (A549), and one fibrosarcoma line (HT-1080) were studied to determine their ability to survive under protein-free conditions. Cells were plated at $5 \times 10^2$ cells per 0.15 cm$^2$ well in 100 µl of DME/5. AFter 72 hours of growth (day 0), medium was replaced with 100 µl of DME/5 mM GLN. Adherent cells were counted with an Artek image analyzer (Dynatech Laboratories, Maclean, Va.) and wells re-fed with protein-free medium. Data presented represent the average of twelve wells counted. The cell lines, WiDr, COLO 201 and COLO 205 can be maintained in long-term culture (more than ten days) when transferred at high density into DME/5 mM GLN (FIG. 3). The SFCM harvested from WiDr cultures at day 21 contained immunochemically detectable amounts of CEA.

EXAMPLE 10

Preparation of HT-29 Cells in Alternative Protein-Free Medium

To prepare the HT-29 cell culture, $5 \times 10^4$ HT-29 cells (per well) were seeded into P24 plates in 1 ml of DME/5 and permitted to grow to confluence (around 3 days). On day 3, medium was aspirated, and cells re-fed with Hanks' Balanced Salt Solution (Whittaker M. A. Bioproducts, Walkersville, Md.) containing 5 mcg/L of amphotericin B, 50 mg/L of gentamycin sulfate and 5 mM of L-glutamine (HBSS-GLN). At two day intervals, triplicate wells were harvested and counted for viability. Remaining wells were aspirated and re-fed with HBSS-GLN mixture.

Total cell number showed only a slight decrease during the first ten days, followed by a precipitous drop in cell number and viability (see Table 4).

TABLE 4.

| HT-29 cells shifted from growth medium into HBSS-GLN mixture | | |
|---|---|---|
| Day | Viable Cells/Well* | % Viable |
| 0 | $1.28 \times 10^5$ | 91 |
| 2 | $1.16 \times 10^5$ | 97 |
| 4 | $1.04 \times 10^5$ | 96 |
| 6 | $0.91 \times 10^5$ | 88 |
| 8 | $0.84 \times 10^5$ | 81 |
| 10 | $0.81 \times 10^5$ | 78 |
| 12 | $0.63 \times 10^5$ | 61 |
| 14 | $0.41 \times 10^5$ | 55 |
| 16 | $0.19 \times 10^5$ | 38 |
| 18 | less than $0.01 \times 10^5$ | 11 |

*Average of 3.

In the foregoing, there has been provided a detailed description of preferred embodiments of the present invention for the purpose of illustration and not limitation. It is to be understood that all other modifications, ramifications and equivalents obvious to those having skill in the art based on this disclosure are intended to be within the scope of the invention as claimed.

We claim:

1. A method of isolating a mammalian tumor-secreted product comprising maintaining mammalian anchorage-dependent colonic adenocarcinoma cells in a maintenance medium containing about 5 mM to about 12 mM of L-glutamine and devoid of exogenous protein for more than ten days and isolating said tumor-secreted product from the medium.

2. A method for maintaining mammalian anchorage-dependent colonic adenocarcinoma cells comprising maintaining said cells in a maintenance medium containing about 5 mM to about 12 mM of L-glutamine and devoid of exogenous protein for more than ten days.

3. The method of claim 7 or 9, wherein said cells are HT-29 cells, WiDr cells, COLO 201 cells or COLO 205 cells.

* * * * *